US011883170B2

(12) United States Patent
Edelhauser

(10) Patent No.: US 11,883,170 B2
(45) Date of Patent: Jan. 30, 2024

(54) BIOLOGICAL FLUID MICRO-SAMPLE MANAGEMENT DEVICE

(71) Applicant: Becton, Dickinson and Company, Franklin Lakes, NJ (US)

(72) Inventor: Adam Edelhauser, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 720 days.

(21) Appl. No.: 17/051,088

(22) PCT Filed: Apr. 30, 2019

(86) PCT No.: PCT/US2019/029912
§ 371 (c)(1),
(2) Date: Oct. 27, 2020

(87) PCT Pub. No.: WO2019/213078
PCT Pub. Date: Nov. 7, 2019

(65) Prior Publication Data
US 2021/0267512 A1    Sep. 2, 2021

Related U.S. Application Data

(60) Provisional application No. 62/665,100, filed on May 1, 2018.

(51) Int. Cl.
*A61B 5/15*    (2006.01)

(52) U.S. Cl.
CPC .. *A61B 5/150755* (2013.01); *A61B 5/150061* (2013.01); *A61B 5/150213* (2013.01); *A61B 5/150351* (2013.01); *A61B 5/15003* (2013.01)

(58) Field of Classification Search
CPC .......... A61B 5/15003; A61B 5/150061; A61B 5/150099; A61B 5/150213;
(Continued)

(56) References Cited

U.S. PATENT DOCUMENTS 5,467,776 A    11/1995   Hamilton
5,743,861 A     4/1998   Columbus et al.
(Continued)

FOREIGN PATENT DOCUMENTS

CN    104825172 A    8/2015
JP    2015154966 A    8/2015
(Continued)

*Primary Examiner* — Eric J Messersmith
(74) *Attorney, Agent, or Firm* — The Webb Law Firm

(57) ABSTRACT

A biological fluid collection device (10) that receives a sample (12) and provides flow-through blood stabilization technology and a precise sample dispensing function for point-of-care and near patient testing applications is disclosed. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications. Advantageously, a biological fluid collection device of the present disclosure includes an internal vacuum (28). In this manner, a biological fluid collection device of the present disclosure eliminates the need for additional vacuum creating components that must be connected to the biological fluid collection device during use.

18 Claims, 16 Drawing Sheets

(58) Field of Classification Search
CPC ........ A61B 5/150221; A61B 5/150351; A61B 5/150755; A61B 5/150992; A61B 5/153; A61B 5/150251; A61B 5/15
See application file for complete search history.

(56) References Cited

U.S. PATENT DOCUMENTS

| | | | |
|---|---|---|---|
| 5,885,240 | A | 3/1999 | Bradbury et al. |
| 9,033,898 | B2 | 5/2015 | Chickerin, III et al. |
| 9,333,283 | B2 | 5/2016 | Cook et al. |
| 10,888,260 | B2 | 1/2021 | Edelhauser et al. |
| 11,076,787 | B2 * | 8/2021 | Bullington ....... A61B 5/150099 |
| 11,259,727 | B2 * | 3/2022 | Bullington ....... A61B 5/150992 |
| 2012/0016308 | A1 | 1/2012 | Schott |
| 2012/0271125 | A1 * | 10/2012 | Bernstein ......... A61B 5/150022 |
| | | | 600/309 |
| 2012/0277696 | A1 * | 11/2012 | Gonzalez-Zugasti ........................ A61B 5/150022 |
| | | | 604/327 |
| 2014/0052022 | A1 * | 2/2014 | Tan .................. A61B 5/150664 |
| | | | 600/579 |
| 2016/0367177 | A1 * | 12/2016 | Edelhauser ...... A61B 5/150221 |
| 2017/0020428 | A1 * | 1/2017 | Rogers .............. A61M 39/0693 |
| 2018/0242890 | A1 | 8/2018 | Chickering, III et al. |

FOREIGN PATENT DOCUMENTS

| | | |
|---|---|---|
| RU | 2092237 C1 | 10/1997 |
| RU | 2586242 C2 | 6/2016 |
| RU | 2603456 C2 | 11/2016 |
| WO | 2010131140 A1 | 11/2010 |
| WO | 2014160804 A2 | 10/2014 |
| WO | 2015189960 A1 | 12/2015 |
| WO | 2016205779 A2 | 12/2016 |

* cited by examiner

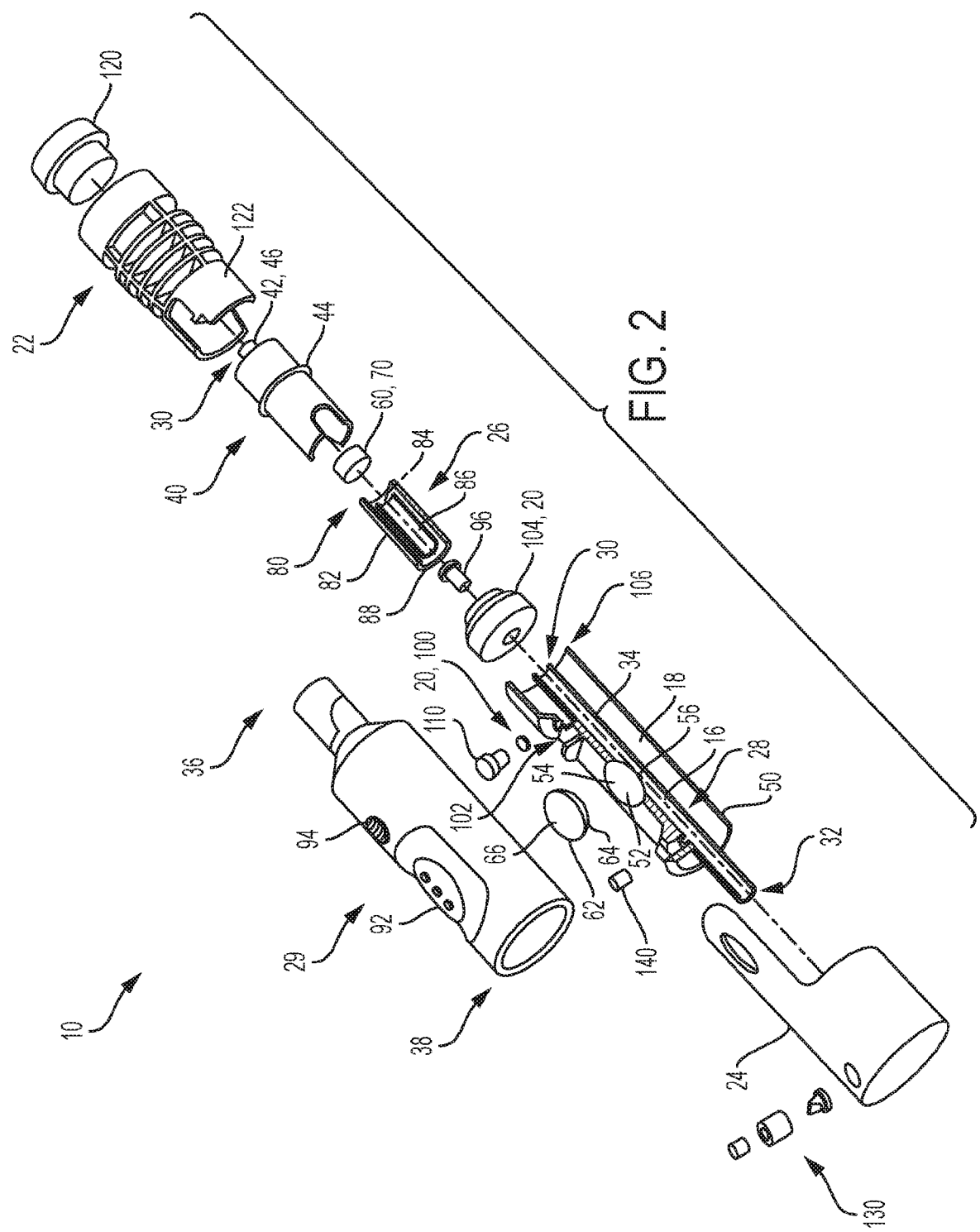

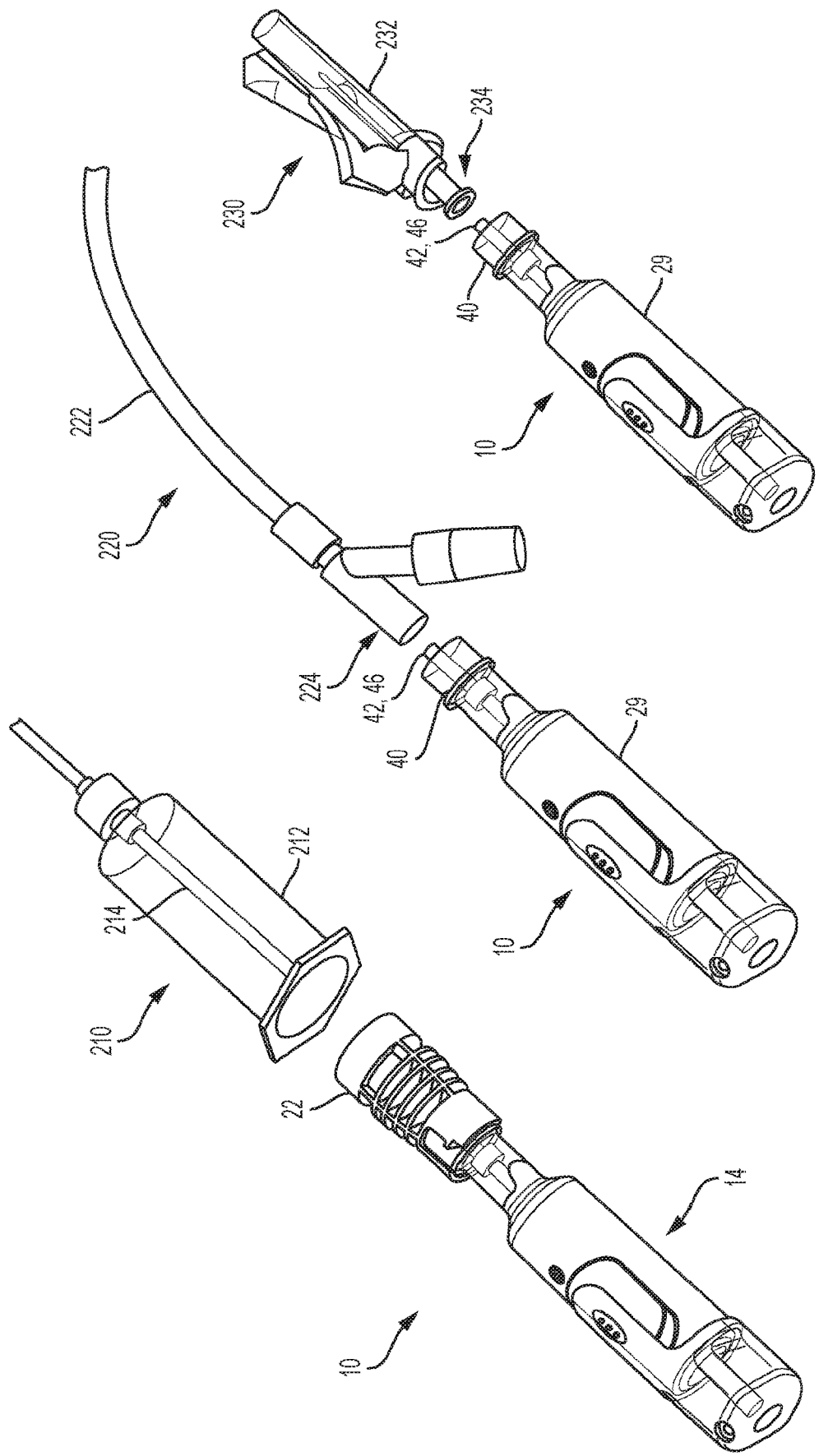

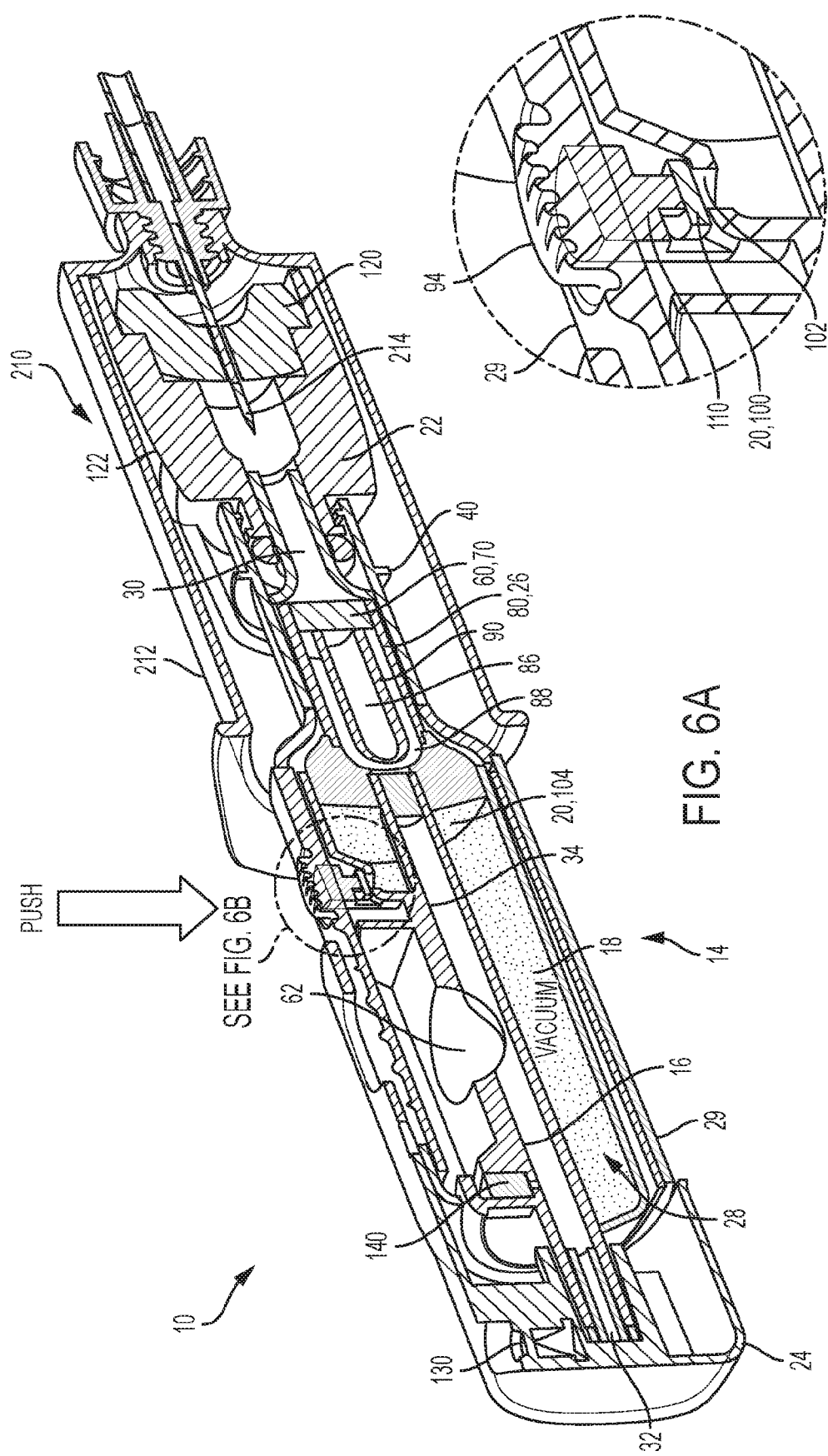

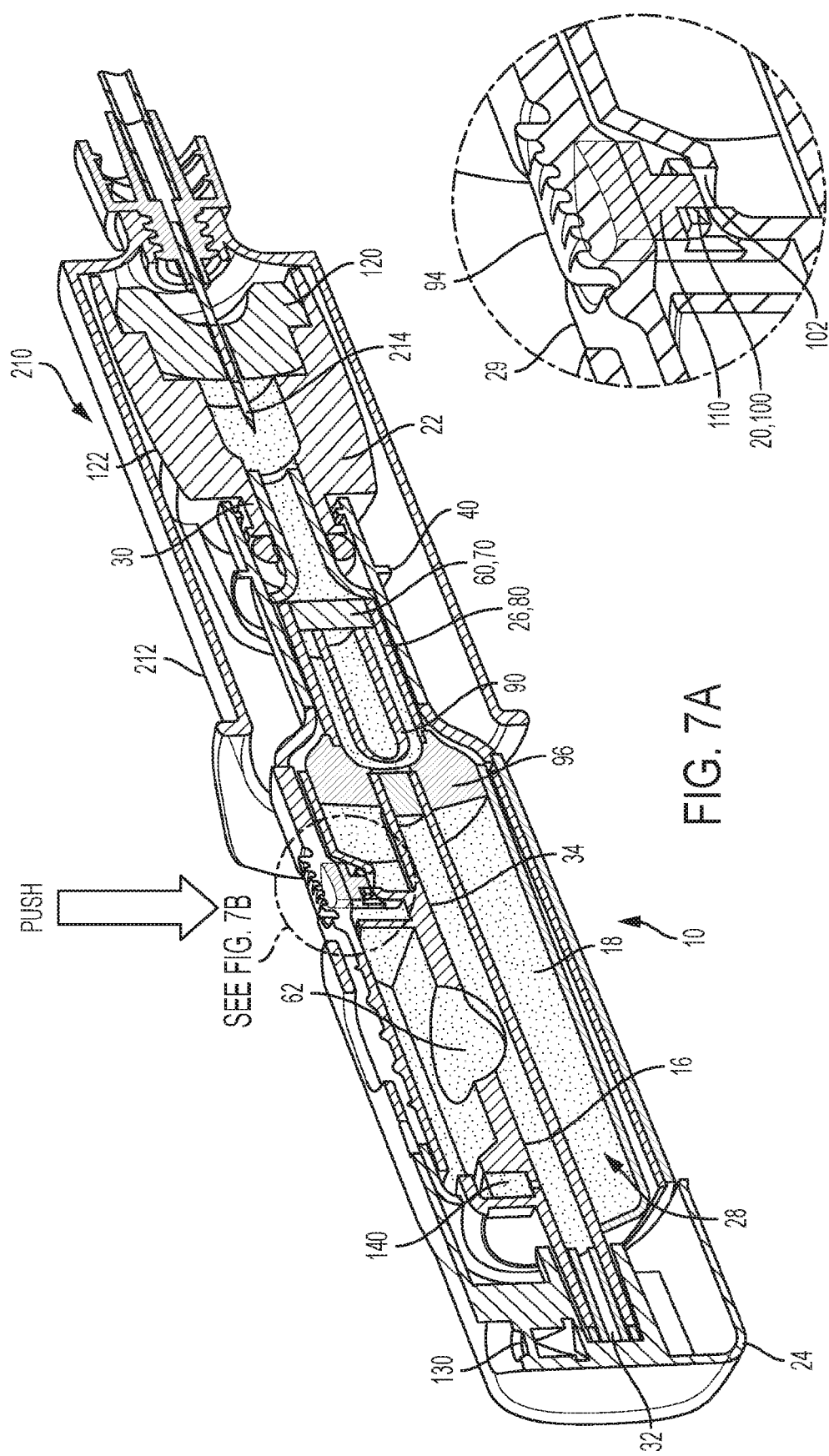

BIOLOGICAL FLUID MICRO-SAMPLE MANAGEMENT DEVICE

CROSS-REFERENCE TO RELATED APPLICATIONS

This application is the United States national phase of International Application No. PCT/US2019/029912, filed Apr. 30, 2019 and claims priority to U.S. Provisional Application Ser. No. 62/665,100, entitled "Biological Fluid Micro-Sample Management Device", and filed May 1, 2018, the entire disclosures of which are hereby incorporated by reference in their entirety.

BACKGROUND OF THE INVENTION

1. Field of the Disclosure

The present disclosure relates generally to a biological fluid collection device. More particularly, the present disclosure relates to a collection module for collecting a small sample of blood and dispensing a portion of the sample into a device for analyzing the sample such as a point-of-care or a near-patient-testing device.

2. Description of the Related Art

A need exists for a device which enables collection of a micro-sample, such as less than 500 microliters of collected sample for analysis, for patient point-of-care applications. Current devices require conventional sample collection and the subsequent use of a 1 ml syringe or pipette to transfer a small blood sample to a point-of-care cartridge or instrument receiving port. Such an open system approach results in an increased blood exposure risk for personnel performing the testing, as well as the collection of excess specimen required for a specified test procedure.

It is therefore desirable to have a blood sample collection and dispensing tool for point-of-care applications which incorporates conventional automatic blood draw and includes a novel controlled sample dispensing capability while minimizing exposure risk.

SUMMARY OF THE INVENTION

The present disclosure provides a biological fluid collection device that receives a sample and provides flow-through blood stabilization technology and a precise sample dispensing function for point-of-care and near patient testing applications. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications.

Advantageously, a biological fluid collection device of the present disclosure provides a consistent blood sample management tool for point-of-care and near patient testing applications, automatic blood draw, passive mixing technology, and controlled small sample dispensing capability to point-of-care cartridge and standard Luer interfaces with near patient testing receiving ports.

Advantageously, a biological fluid collection device of the present disclosure includes an internal vacuum. In this manner, a biological fluid collection device of the present disclosure eliminates the need for additional vacuum creating components that must be connected to the biological fluid collection device during use. In one embodiment, an evacuated chamber of the biological fluid collection device has a vacuum that draws a sample within a collection chamber. A user of the biological fluid collection device is able to control when the internal vacuum is applied.

In accordance with an embodiment of the present invention, a biological fluid collection device adapted to receive a sample includes a housing having an inlet, an outlet, and a passageway extending between the inlet and the outlet; a collection chamber inside the housing and in fluid communication with the passageway; an evacuated chamber inside the housing and containing a vacuum; and a seal transitionable from a closed position in which the vacuum is enclosed within the evacuated chamber to an open position in which the vacuum is applied to the inlet to draw the sample within the collection chamber.

In one configuration, the seal includes a foil element disposed on a first portion of the collection chamber, and a stopper element disposed on a second portion of the collection chamber. In another configuration, the biological fluid collection device includes an activation member transitionable between a first position and a second position in which the activation member pierces the foil element to move the seal to the open position. In yet another configuration, the biological fluid collection device includes a closure covering the inlet of the housing. In one configuration, the biological fluid collection device includes a cap covering the outlet of the housing and having a venting portion. In another configuration, the venting portion allows air to pass therethrough and prevents the sample from passing therethrough. In yet another configuration, the biological fluid collection device includes a film having an inferior surface and a superior surface, the film transitionable between an initial position in which the inferior surface of the film is in contact with a portion of the collection chamber and a fill position in which the inferior surface of the film is spaced from the collection chamber. In one configuration, with the film in the fill position, the collection chamber is filled with the sample. In another configuration, as the collection chamber fills with the sample, the film is transitioned to the fill position. In yet another configuration, the biological fluid collection device includes a deformable portion transitionable between an initial position in which the sample is contained within the collection chamber and a deformed position in which the deformable portion contacts the superior surface of the film and a portion of the sample is expelled from the outlet of the collection chamber. In one configuration, the biological fluid collection device includes a mixing chamber disposed between the inlet and the collection chamber; and a sample stabilizer disposed between the inlet and the mixing chamber. In another configuration, the mixing chamber receives the sample and the sample stabilizer therein. In yet another configuration, the mixing chamber effectuates distributed mixing of the sample stabilizer within the sample. In one configuration, the biological fluid collection device includes a material including pores disposed between the inlet and the mixing chamber, and a dry anticoagulant powder within the pores of the material. In another configuration, the sample dissolves and mixes with the dry anticoagulant powder while passing through the material. In yet another configuration, the material is an open cell foam. In one configuration, the sample stabilizer is the dry anticoagulant powder. In another configuration, the sample is a blood sample.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 2 is an exploded, perspective view of a biological fluid collection device in accordance with an embodiment of the present invention.

FIG. 4A is a perspective view of a biological fluid collection device with a closure being connected to a first blood collection device in accordance with an embodiment of the present invention.

FIG. 4B is a perspective view of a biological fluid collection device being connected to a second blood collection device in accordance with an embodiment of the present invention.

FIG. 4C is a perspective view of a biological fluid collection device being connected to a third blood collection device in accordance with an embodiment of the present invention.

FIG. 6A is a cross-sectional side elevation view of a biological fluid collection device with a closure connected to a first blood collection device with an activation member in a first position in accordance with an embodiment of the present invention.

FIG. 6B is an enlarged partial cross-sectional view of the biological fluid collection device taken along section 6B of FIG. 6A in accordance with an embodiment of the present invention.

FIG. 7A is a cross-sectional side elevation view of a biological fluid collection device with a closure connected to a first blood collection device with an activation member in a second position in accordance with an embodiment of the present invention.

FIG. 7B is an enlarged partial cross-sectional view of the biological fluid collection device taken along section 7B of FIG. 7A in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
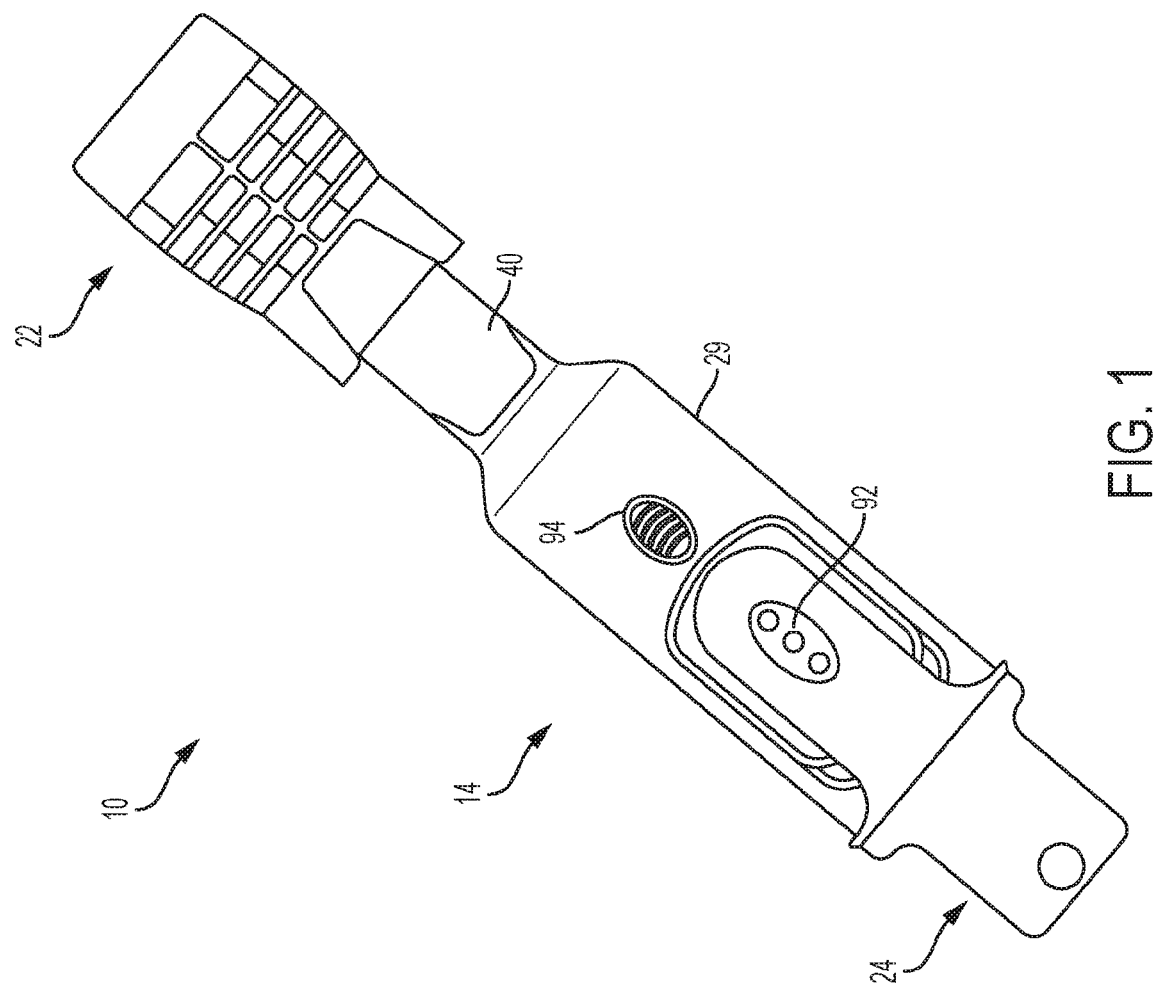
FIG. 1 is a side elevation view of a biological fluid collection device in accordance with an embodiment of the present invention.
Figure 3B:
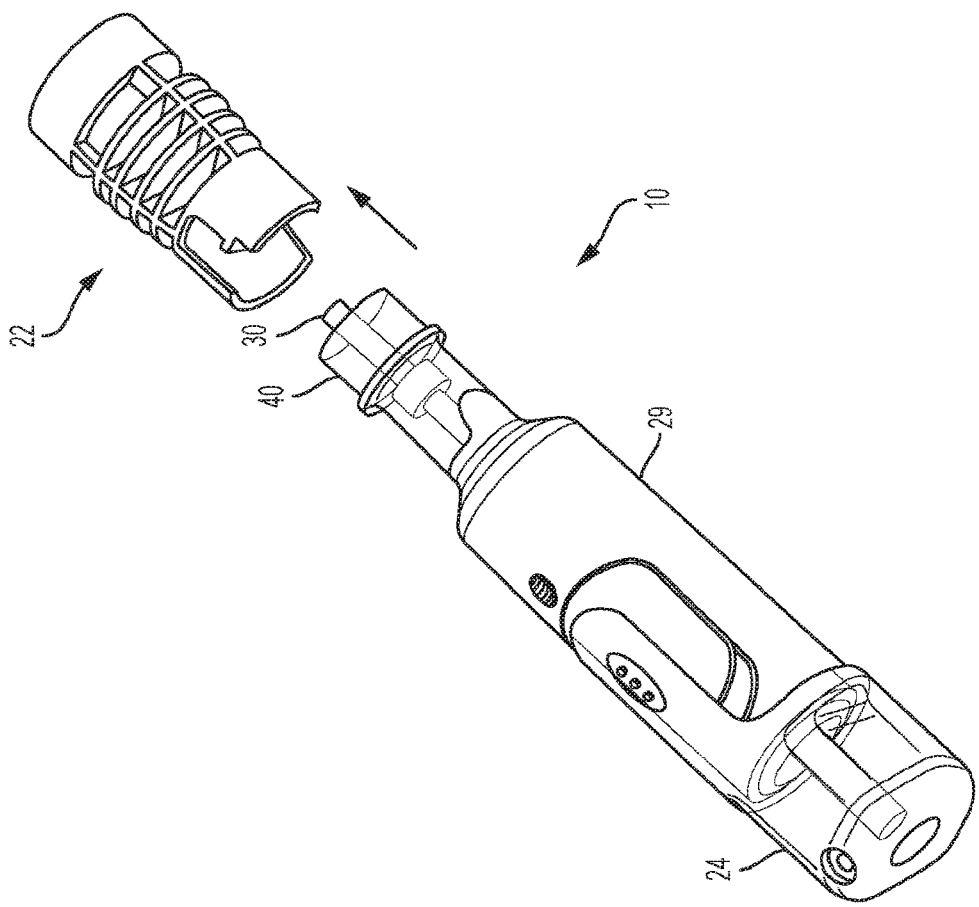
FIG. 3B is a perspective view of a biological fluid collection device with a closure removed therefrom in accordance with an embodiment of the present invention.
Figure 3A:
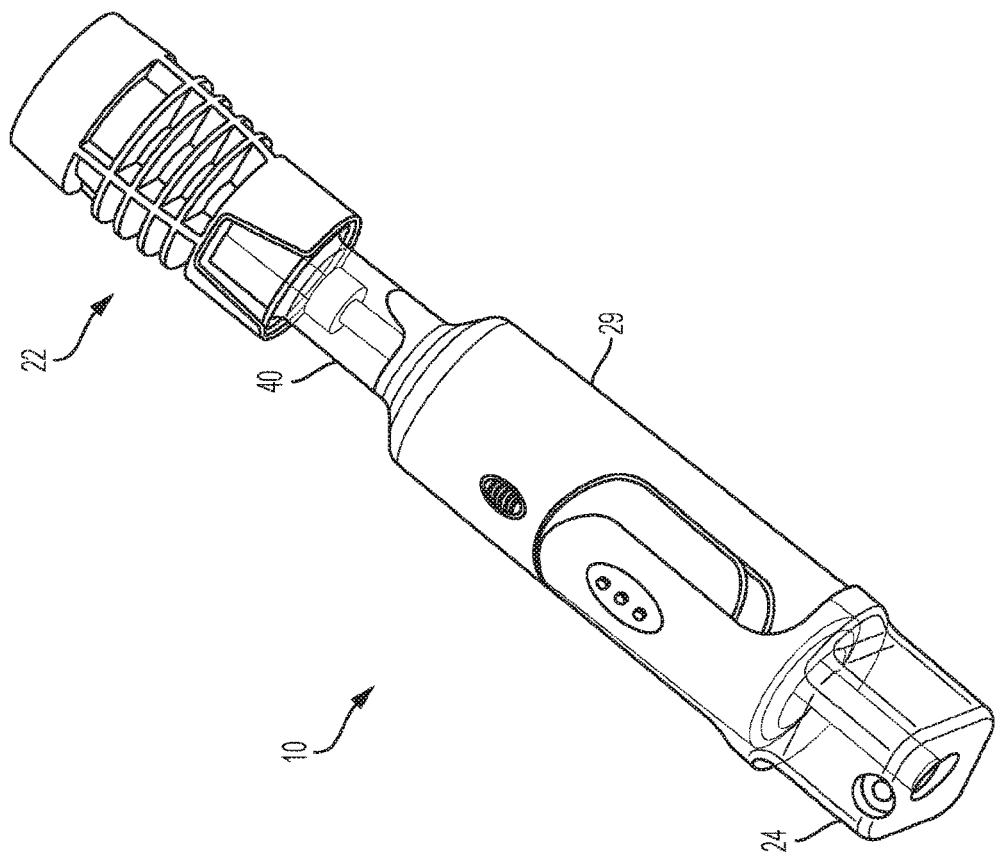
FIG. 3A is a perspective view of a biological fluid collection device with a closure connected thereto in accordance with an embodiment of the present invention.
Figure 5:
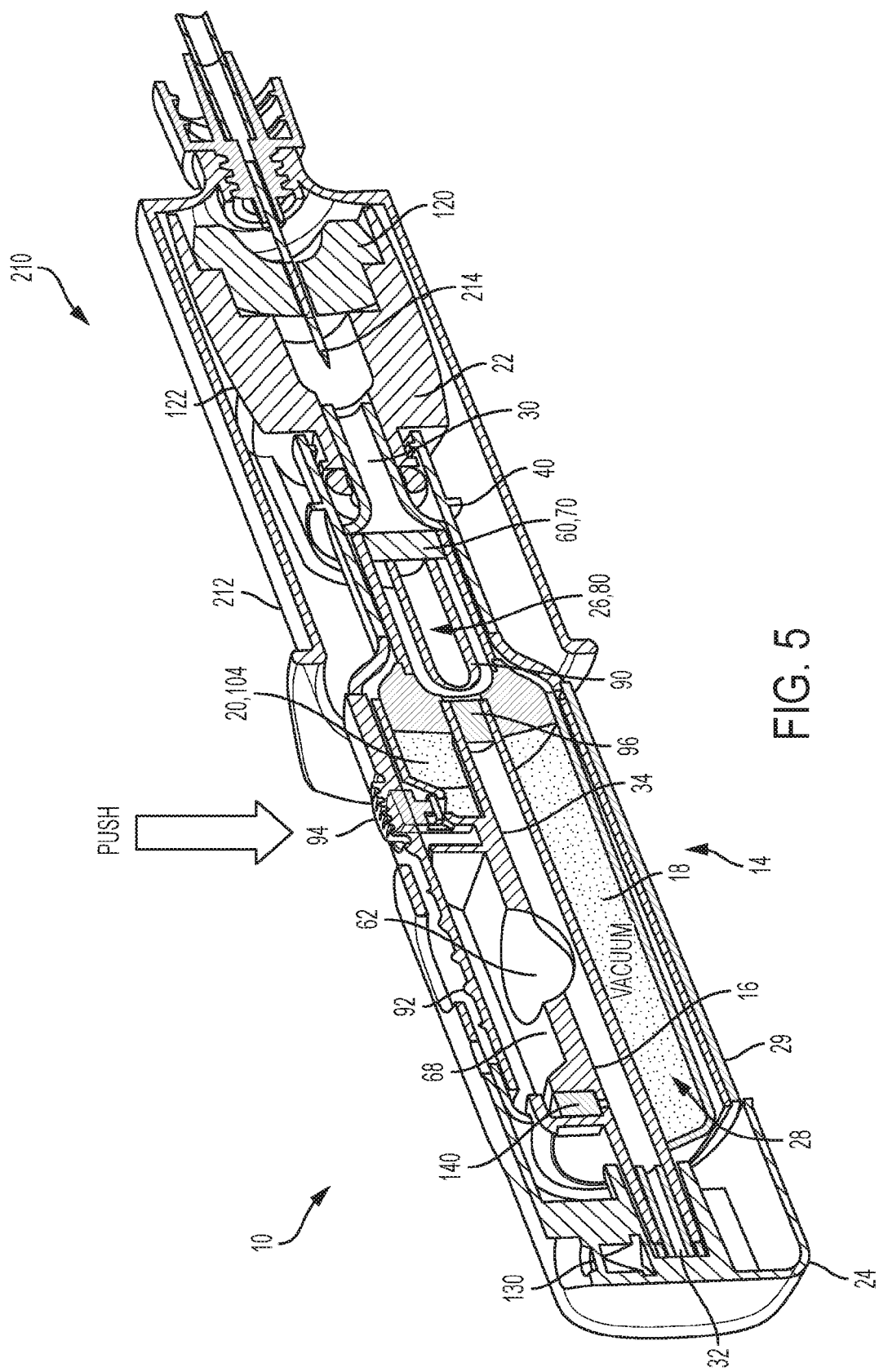
FIG. 5 is a cross-sectional side elevation view of a biological fluid collection device with a closure connected to a first blood collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a biological fluid collection device that receives a sample and provides flow-through blood stabilization technology and a precise sample dispensing function for point-of-care and near patient testing applications. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications.

Advantageously, a biological fluid collection device of the present disclosure provides a consistent blood sample management tool for point-of-care and near patient testing applications, automatic blood draw, passive mixing technology, and controlled small sample dispensing capability to point-of-care cartridge and standard Luer interfaces with near patient testing receiving ports.

Advantageously, a biological fluid collection device of the present disclosure includes an internal vacuum. In this manner, a biological fluid collection device of the present disclosure eliminates the need for additional vacuum creating components that must be connected to the biological fluid collection device during use. In one embodiment, an evacuated chamber of the biological fluid collection device has a vacuum that draws a sample within a collection chamber. A user of the biological fluid collection device is able to control when the internal vacuum is applied.

FIGS. 1-5 illustrate an exemplary embodiment of a biological fluid collection device of the present disclosure. Referring to FIGS. 1-5, a biological fluid collection device 10 of the present disclosure is adapted to receive a biological fluid sample 12, such as a blood sample, and includes a housing or housing assembly 14, a collection chamber 16, an evacuated chamber 18, a seal or seal assembly 20, a closure 22, a cap 24, and a mixing assembly 26.

Advantageously, a biological fluid collection device 10 of the present disclosure includes an evacuated chamber 18 inside the housing 14 and containing a vacuum 28 internal to the biological fluid collection device 10.

In one embodiment, the housing or housing assembly 14 of the biological fluid collection device 10 includes a primary housing 29 having an inlet 30, an outlet 32, and a passageway 34 extending between the inlet 30 and the outlet 32. In one embodiment, the inlet 30 is located at a first end 36 of the primary housing 29 and the outlet 32 is located at a second end 38 of the primary housing 29. The inlet 30 and the outlet 32 are in fluid communication via the passageway 34 extending therebetween.

In one embodiment, the housing 14 may also include a connector housing 40 secured to the first end 36 of the primary housing 29. The connector housing 40 includes a connector housing interface 42 and a flange 44. In one embodiment, the connector housing interface 42 includes a male Luer fitting 46 that can be used to connect the biological fluid collection device 10 to a second blood collection device 220 via a standard Luer interface 224 or to a third blood collection device 230 via a standard Luer interface 234, as shown in FIGS. 4A-4C and as described in more detail below. In one embodiment, with a connector housing 40 secured to the first end 36 of the primary housing 29, the inlet 30 of the biological fluid collection device 10 is located at the interface 42 of the connector housing 40.

In one embodiment, the biological fluid collection device 10 includes a collection chamber 16 inside the housing 14 and in fluid communication with the passageway 34, an evacuated chamber 18 inside the housing 14 and containing a vacuum 28, and a mixing assembly 26. In one embodiment, the housing assembly 14 includes an interior housing 50 inside the primary housing 29. In one embodiment, the interior housing 50 defines the collection chamber 16 and the evacuated chamber 18.

Advantageously, a biological fluid collection device 10 of the present disclosure includes the evacuated chamber 18 inside the housing 14 and containing a vacuum 28 internal to the biological fluid collection device 10. The evacuated chamber 18 containing a vacuum 28 of the present disclosure eliminates the need for additional vacuum creating components that must be connected to the biological fluid collection device 10 during use.

The evacuated chamber 18 of the biological fluid collection device 10 has a vacuum 28 that draws a sample 12 within the collection chamber 16. A user of the biological fluid collection device 10 is able to control when the internal vacuum 28 is applied as described in more detail below.

The biological fluid collection device 10 includes a seal or seal assembly 20 that is transitionable from a closed position (FIGS. 5-6B) in which the vacuum 28 is enclosed within the evacuated chamber 18 to an open position (FIGS. 7A-8D) in which the vacuum 28 is applied to the passageway 34 and the inlet 30 of the biological fluid collection device 10 to draw a sample 12 within the biological fluid collection device 10.

Referring to FIG. 2, in one embodiment, the seal 20 includes a foil element 100 disposed on a first portion of the evacuated chamber 18. For example, in one embodiment, the foil element 100 seals an aperture 102 within a wall of the evacuated chamber 18. The seal 20 may also include a stopper element 104 disposed on a second portion of the evacuated chamber 18. For example, in one embodiment, the stopper element 104 may seal a first end 106 of the interior housing 50.

In one embodiment, the stopper element 104 may be a unitary device molded of any flexible, elastomeric material conventionally used for sealing. In particular, the stopper element 104 may be formed of an elastomeric material including rubber, silicone based elastomer, and thermoplastic elastomer, or similar materials.

The biological fluid collection device 10 includes an activation member 110 that is transitionable between a first position (FIGS. 5-6B) and a second position (FIGS. 7A-8D) in which the activation member 110 pierces the foil element 100 to move the seal 20 to the open position (FIGS. 7A-8D). With the seal 20 in the open position, the vacuum 28 contained within the evacuated chamber 18 is applied to the inlet 30 and passageway 34 to draw a sample 12 within the collection chamber 16. In this manner, the vacuum 28 contained within the evacuated chamber 18 is placed in communication with the collection chamber 16 and passageway 34 of the biological fluid collection device 10 via the open aperture 102 and the vacuum 28 of the evacuated chamber 18 draws a sample 12 within the collection chamber 16 of the biological fluid collection device 10.

In one embodiment, the activation member 110 is disposed within the biological fluid collection device 10 between a second deformable portion 94 of primary housing 29 and the foil element 100 that seals the aperture 102 within a wall of the evacuated chamber 18. In this manner, referring to FIGS. 7A and 7B, in one embodiment, a user may push down the second deformable portion 94 so that the second deformable portion 94 contacts and pushes down the activation member 110 to the second position (FIGS. 7A-8D) in which the activation member 110 pierces the foil element 100 to move the seal 20 to the open position (FIGS. 7A-8D). The activation member 110 allows a user of the biological fluid collection device 10 to be able to control when the internal vacuum 28 is applied to draw a sample 12 within the collection chamber 16 of the biological fluid collection device 10.

The mixing assembly 26 and the collection chamber 16 are provided in fluid communication with the passageway 34. The mixing assembly 26 and the collection chamber 16 are positioned such that a biological fluid sample 12, such as a blood sample, introduced into the inlet 30 of the biological fluid collection device 10 will first pass through a sample stabilizer 60, then the blood sample 12 and the sample stabilizer 60 pass through the mixing assembly 26, and subsequently the sample 12 with the sample stabilizer 60 properly mixed therein flow into the collection chamber 16, prior to reaching the outlet 32 of the biological fluid collection device 10. In this way, the blood sample 12 may be mixed with a sample stabilizer 60, such as an anticoagulant or other additive, provided within the biological fluid collection device 10 before passing through the mixing assembly 26 for proper mixing of the sample stabilizer 60 within the blood sample 12, and then the stabilized sample is received and stored within the collection chamber 16.

In one embodiment, a sample stabilizer 60 is disposed between the inlet 30 of connector housing 40 of housing assembly 14 and the mixing assembly 26. The biological fluid collection device 10 of the present disclosure provides passive and fast mixing of a blood sample 12 with the sample stabilizer 60. For example, the biological fluid collection device 10 includes a mixing assembly 26 that allows for passive mixing of the blood sample 12 with an anticoagulant or another additive, such as a blood stabilizer, as the blood sample 12 flows through the mixing assembly 26.

The sample stabilizer 60 can be an anticoagulant, or a substance designed to preserve a specific element within the blood such as, for example, RNA, protein analyte, or other element. In one embodiment, the sample stabilizer 60 is disposed between the inlet 30 and the mixing assembly 26. In other embodiments, the sample stabilizer 60 may be disposed in other areas within the housing 14 of the biological fluid collection device 10.

Figure 13:
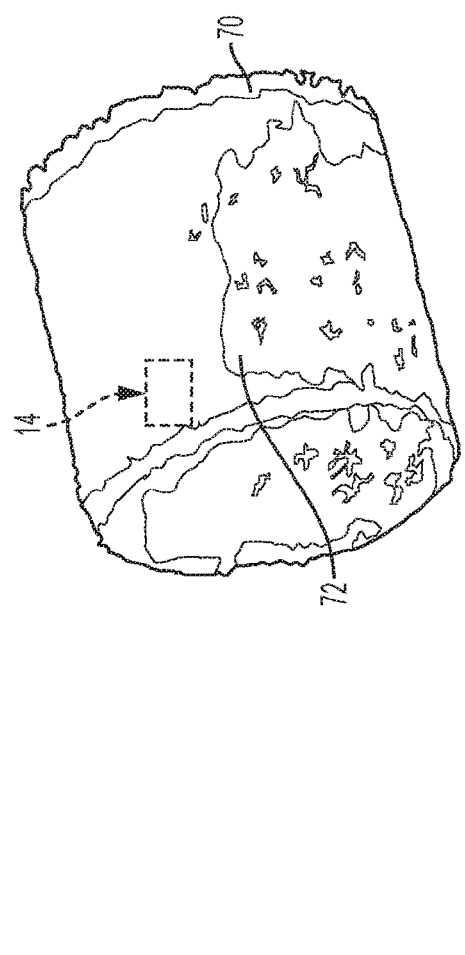
FIG. 13 is a perspective view of an open cell foam material in accordance with an embodiment of the present invention.
Figure 14:
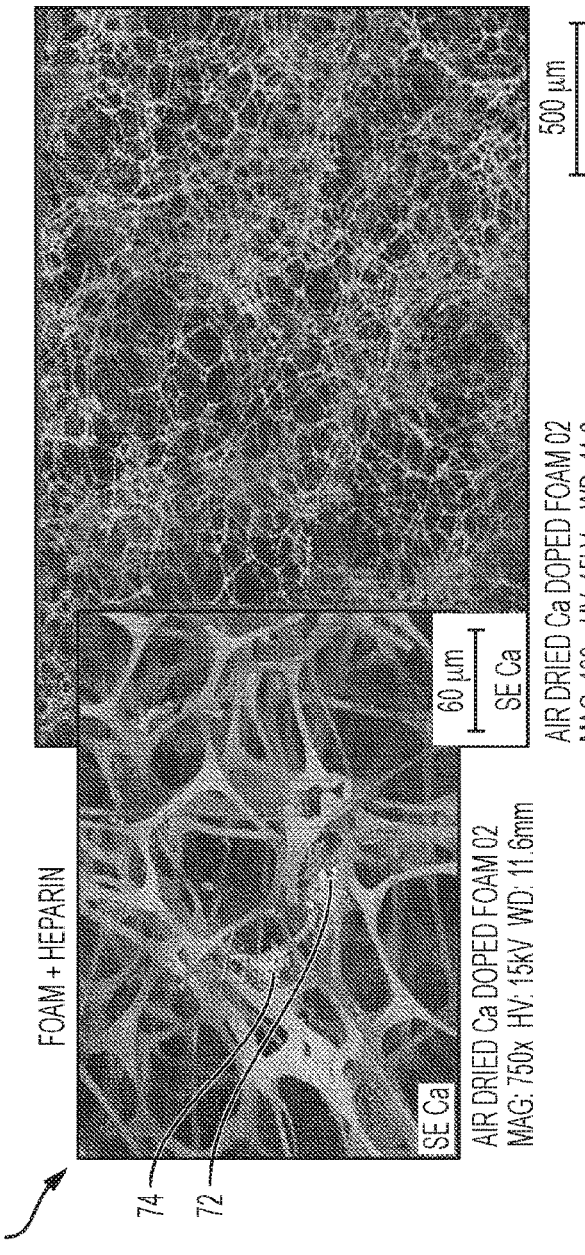
FIG. 14 is a microscopic view of the microstructure of an open cell foam material having a dry anticoagulant powder distributed throughout its microstructure in accordance with an embodiment of the present invention.

Referring to FIGS. 13 and 14, in one embodiment, the biological fluid collection device 10 includes a material 70 including pores 72 and a dry anticoagulant powder 74 that is within the pores 72 of the material 70. In one embodiment, the material 70 is disposed between the inlet 30 of connector housing 40 of housing assembly 14 and the mixing assembly 26. In this manner, the biological fluid collection device 10 may include a dry anticoagulant, such as Heparin or EDTA, deposited on or within a portion of the biological fluid collection device 10. In one embodiment, the material 70 is an open cell foam that contains dry anticoagulant dispersed within the cells of the open cell foam to promote the effectiveness of the flow-through mixing and anticoagulant uptake. In one embodiment, the sample stabilizer 60 is the dry anticoagulant powder 74.

In one embodiment, the open cell foam may be treated with an anticoagulant to form a dry anticoagulant powder 74 finely distributed throughout the pores 72 of the open cell foam. As the blood sample 12 enters the biological fluid collection device 10, the blood sample 12 passes through the open cell foam and is exposed to the anticoagulant powder 74 available throughout the internal pore structure of the open cell foam. In this manner, the sample 12 dissolves and mixes with the dry anticoagulant powder 74 while passing through the material 70 or open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

The biological fluid collection device 10 includes a mixing assembly 26 that allows for passive mixing of the blood sample 12 with an anticoagulant or another additive, such as a blood stabilizer, as the blood sample 12 flows through the mixing assembly 26. In one embodiment, the mixing assembly 26 is disposed between the inlet 30 and the outlet 32.

The internal portion of the mixing assembly 26 may have any suitable structure or form as long as it provides for the mixing of the blood sample 12 with an anticoagulant or another additive as the blood sample 12 passes through the passageway 34 of the biological fluid collection device 10. In one embodiment, the mixing assembly 26 includes a mixing chamber 80 having an outer wall 82 and an inner wall 84 that defines an inner channel 86. The mixing chamber 80 also includes an outer channel 88 defined between the outer wall 82 and the inner wall 84. In one embodiment, the mixing chamber 80 is disposed between the inlet 30 and the collection chamber 16.

In one embodiment, the inner wall 84 includes an exit aperture 90. In one embodiment, the cross-sectional area of the exit aperture 90 is sized to control the flow of the blood sample 12 and the sample stabilizer 60 through the mixing assembly 26 for distributed mixing. As a blood sample 12 enters the biological fluid collection device 10, the blood sample 12 will first pass through a sample stabilizer 60, then the blood sample 12 and the sample stabilizer 60 enter the mixing assembly 26 or mixing chamber 80 for controlled distributed mixing. For example, the first portion of the blood sample 12 with sample stabilizer 60 that enters the mixing assembly 26 flows through the inner channel 86. Once the inner channel 86 is full, subsequent portions of the blood sample 12 with sample stabilizer 60 that enters the mixing assembly 26 will flow to the outer channel 88. The reduced cross-sectional area of the exit aperture 90 decreases the flow rate of the blood sample 12 with sample stabilizer 60 out the inner channel 86. In this manner, the first portion of the blood sample 12 with the sample stabilizer 60 within the inner channel 86 flows out the exit aperture 90 of the inner channel 86 at a controlled rate back into the mixing chamber 80 for controlled distributed mixing with the subsequent portions of the blood sample 12 with sample stabilizer 60 flowing through the outer channel 88.

In one embodiment, the biological fluid collection device 10 includes a valve 96 that may be used to control the flow of the blood sample 12 and the sample stabilizer 60 through the mixing assembly 26 for distributed mixing.

The mixing chamber 80 receives the sample 12 and the sample stabilizer 60 therein, and effectuates distributed mixing of the sample stabilizer 60 within the sample 12. The mixing chamber 80 effectuates distributed mixing of the sample stabilizer 60 within the sample 12 and prevents a very high sample stabilizer concentration in any portion of the blood sample 12. This prevents underdosing of the sample stabilizer 60 in any portion of the blood sample 12. The mixing chamber 80 effectuates distributed mixing of the sample stabilizer 60 within the sample 12 so that an approximately equal amount and/or concentration of the sample stabilizer 60 is dissolved throughout the blood sample 12, e.g., an approximately equal amount and/or concentration of the sample stabilizer 60 is dissolved into the blood sample 12 from a front portion of the blood sample 12 to a rear portion of the blood sample 12.

In one embodiment, the biological fluid collection device 10 includes a collection chamber 16 that is disposed between the mixing assembly 26 and the outlet 32. In one embodiment, the collection chamber 16 includes a cavity 52 having a cavity superior surface 54 and a cavity inferior surface 56.

The biological fluid collection device 10 includes a film 62 having an inferior surface 64, a superior surface 66, a dome portion 67, and a flange portion 68. In one configuration, the film 62 forms a chamber 69 (FIGS. 8D and 9) as described in more detail below. In one embodiment, the film 62 is transitionable between an initial position (FIG. 5) in which the inferior surface 64 of the film 62 is in contact with a portion of the collection chamber 16, e.g., the superior surface 54 of the cavity 52, and a fill position (FIGS. 8D and 9) in which the inferior surface 64 of the film 62 is spaced from the collection chamber 16, e.g., the cavity 52. In one embodiment, with the film 62 in the fill position, the collection chamber 16 is filled with the sample 12 as described in more detail below. As described below, as the collection chamber 16 fills with the sample 12, the film 62 is transitioned to the fill position.

In one embodiment, the flange portion 68 of the film 62 allows the film 62 to be securely positioned to a portion of the interior housing 50 within the biological fluid collection device 10. In one embodiment, the film 62 is a thin, flexible film that allows for a preevacuated blood collection chamber.

Figure 9:
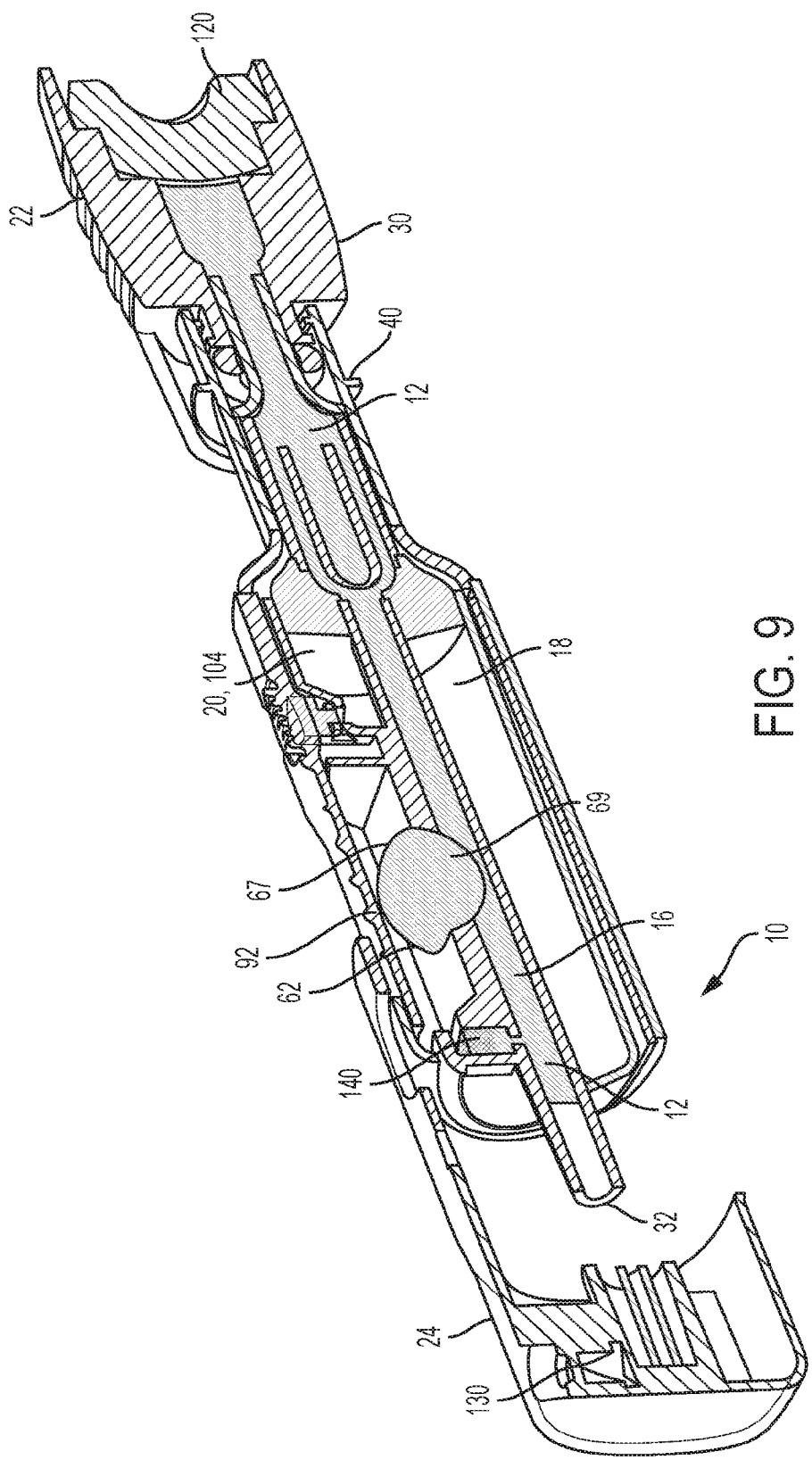
FIG. 9 is a cross-sectional side elevation view of a biological fluid collection device with a cap being removed and a deformable portion in an initial position in accordance with an embodiment of the present invention.
Figure 10:
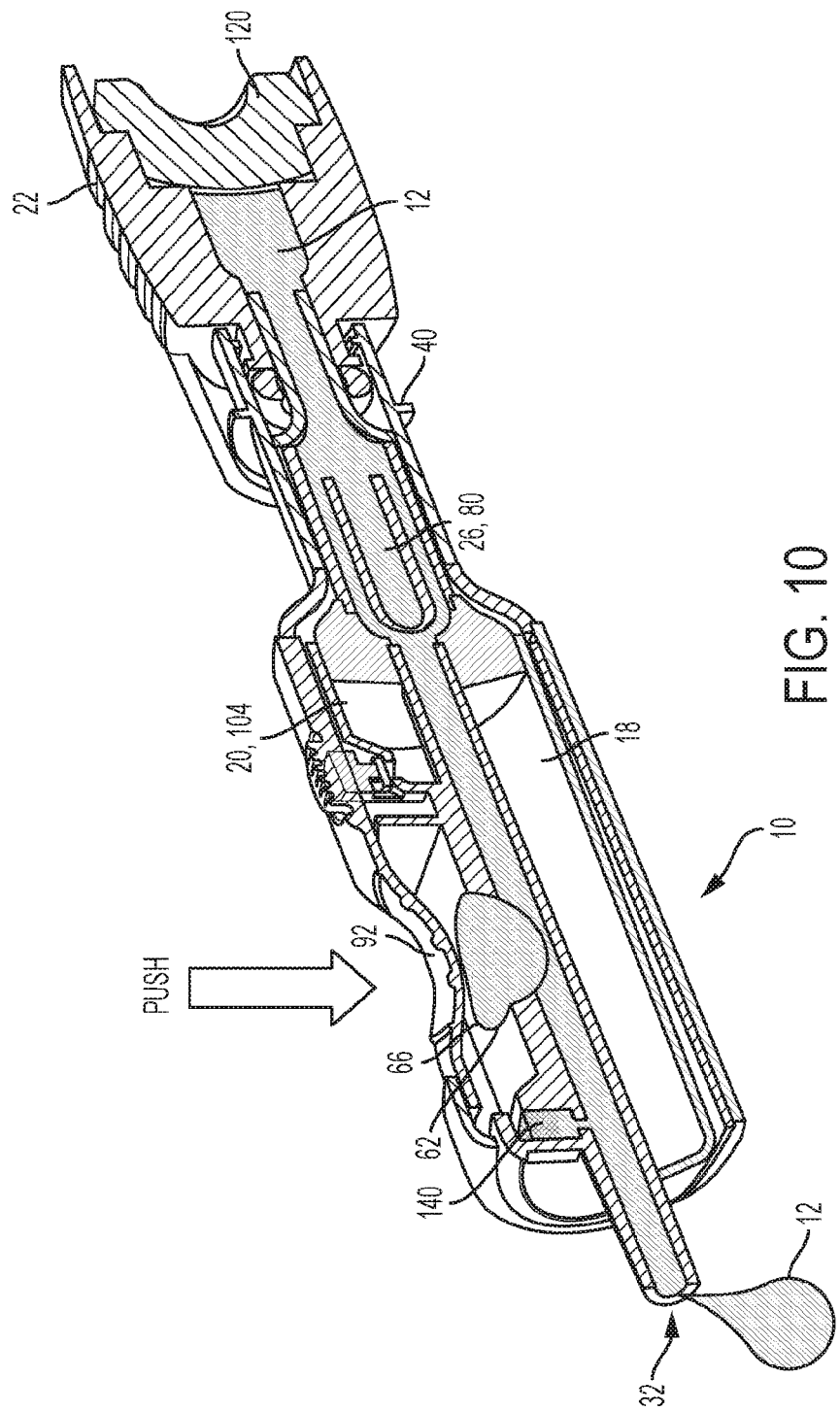
FIG. 10 is a cross-sectional side elevation view of a biological fluid collection device with a deformable portion in a deformed position in accordance with an embodiment of the present invention.

In one embodiment, the biological fluid collection device 10 includes a deformable portion 92 that is transitionable between an initial position (FIG. 9) in which the sample 12 is contained within the collection chamber 16 and a deformed position (FIG. 10) in which the deformable portion 92 contacts the superior surface 66 of the film 62 and a portion of the sample 12 is expelled from the outlet 32 of the collection chamber 16.

In one embodiment, the deformable portion 92 is located on a portion of the primary housing 29. In one embodiment, the biological fluid collection device 10 also includes a second deformable portion 94 located on a portion of the primary housing 29 spaced from the deformable portion 92.

Advantageously, by having a deformable portion 92, a biological fluid collection device 10 of the present disclosure is able to dispense sample 12 out of the collection chamber 16 and the outlet 32 in a controlled manner.

After passing through the mixing assembly 26, the stabilized sample is directed to the collection chamber 16. The collection chamber 16 may take any suitable shape and size to store a sufficient volume of blood necessary for the desired testing, for example 500 µl or less.

The deformable portion 92 and the second deformable portion 94 may be made of any material that is flexible, deformable, and capable of providing a fluid tight seal with the collection chamber 16. In some embodiments, the deformable portion 92 and the second deformable portion 94 may be made of natural or synthetic rubber, and other suitable elastomeric materials. The deformable portion 92 and the second deformable portion 94 are secured to a portion of the primary housing 29 such that the deformable portion 92 and the second deformable portion 94 are transitionable between an initial position and a deformed position.

In one embodiment, the biological fluid collection device 10 includes a closure 22 covering the inlet 30 of the housing 14. For example, the closure 22 is engaged with the inlet 30 of connector housing 40 of the housing 14 to seal the passageway 34. The closure 22 protectively covers the inlet 30. The closure 22 allows for introduction of a blood sample 12 into the passageway 34 of the housing 14 and may include a pierceable self-sealing stopper 120 with an outer shield 122 such as a Hemogard™ cap commercially available from Becton, Dickinson and Company.

Advantageously, the biological fluid collection device 10 of the present disclosure allows for direct Luer access without the use of an LLAD (Luer Line Access Device) or any other holder.

Advantageously, a biological fluid collection device 10 of the present disclosure can be engaged with many different sources through which biological fluid, such as a blood sample 12, is passed. For example, referring to FIGS. 4A-4C, a biological fluid collection device 10 of the present disclosure allows for connection to multiple different blood collection devices. Referring to FIG. 4A, in a first configuration, with a closure 22 engaged with the housing 14 to seal the inlet 30 and the passageway 34 of the biological fluid collection device 10, the biological fluid collection device 10 may be connected to a first blood collection device 210. In one embodiment, the first blood collection device 210 includes a tube holder 212 having a needle cannula 214.

Referring to FIG. 4B, in a second configuration, with a closure 22 removed from the housing 14 of the biological fluid collection device 10, the biological fluid collection device 10 may be connected to a second blood collection device 220. In one embodiment, the second blood collection device 220 includes a line 222 having a Luer interface 224.

Referring to FIG. 4C, in a third configuration, with a closure removed from the housing 14 of the biological fluid collection device 10, the biological fluid collection device 10 may be connected to a third blood collection device 230. In one embodiment, the third blood collection device 230 includes an arterial blood collection device 232 having a Luer interface 234.

Advantageously, a biological fluid collection device 10 of the present disclosure enables a user to connect directly to a Luer-line, e.g., IV Catheter, wingset, PICC, or similar device without the use of an LLAD (Luer Line Access Device) or any other holder. As discussed above, with a closure 22 engaged with the housing 14 to seal the inlet 30 and the passageway 34 of the biological fluid collection device 10, a user may connect the biological fluid collection device 10 to a conventional tube holder. With the closure removed from the housing 14 of the biological fluid collection device 10, a user may connect the biological fluid collection device 10 to a Luer interface using the connector housing interface 42.

In one embodiment, the biological fluid collection device 10 includes a cap 24 covering the outlet 32 of the housing 14 and having a venting portion or venting plug 130. The cap 24 is removably attachable to the outlet 32 and protectively covers the outlet 32. In one embodiment, the venting portion 130 of the cap 24 allows air to pass therethrough and prevents the sample 12 from passing therethrough.

The construction of the cap 24 and venting portion 130 allows air to pass through the cap 24 while preventing the blood sample 12 from passing through the cap 24 and may include a hydrophobic filter or valve. The venting portion 130 has selected air passing resistance that may be used to finely control the filling rate of the passageway 34 and/or the collection chamber 16 of the biological fluid collection device 10. By varying the porosity of the venting portion 130, the velocity of the air flow out of the cap 24, and thus the velocity of the blood sample flow into the biological fluid collection device 10, may be controlled.

In one embodiment, the biological fluid collection device 10 includes a plug or vent 140. In one embodiment, the plug 140 may be formed of a material having pores. The pores allow air to evacuate the biological fluid collection device 10 as described in more detail below. In one embodiment, the biological fluid collection device 10 may include one plug 140. In other embodiments, the biological fluid collection device 10 may include more than one plug 140.

Referring to FIGS. 4A-10, use of a biological fluid collection device 10 of the present disclosure will now be described. Referring to FIGS. 4A-4C, a user can select one of the ways, sources, or methods that the biological fluid collection device 10 is able to receive a blood sample. For example, the biological fluid collection device 10 of the present disclosure allows a blood sample to be received from a variety of sources including, but not limited to, a first blood collection device 210 (FIGS. 4A and 5-8D), a second blood collection device 220 (FIG. 4B), a third blood collection device 230 (FIGS. 4C and 11-12), or other blood collection device.

Referring to FIGS. 4A and 5-8D, in a first configuration, with a closure 22 engaged with the housing 14 to seal the inlet 30 and the passageway 34 of the biological fluid collection device 10, the biological fluid collection device 10 may be connected to a first blood collection device 210. In one embodiment, the first blood collection device 210 includes a tube holder 212 having a needle cannula 214.

In use, a needle cannula 214 of tube holder 212 is inserted into the passageway 34 of the housing 14 of the biological fluid collection device 10 through the inlet 30, such as through the pierceable self-sealing stopper 120 of closure 22. As shown in FIGS. 5-8D, the biological fluid collection device 10 may be inserted into a conventional tube holder 212 having a cannula 214 through which biological fluid, such as a blood sample 12, is passed.

The blood sample 12 is pulled into the passageway 34 of the housing 14 of the biological fluid collection device 10 from the conventional tube holder 102 by the draw of the vacuum 28 contained in the evacuated chamber 18. A user of the biological fluid collection device 10 is able to control when the internal vacuum 28 of the biological fluid collection device 10 is applied.

For example, referring to FIGS. 7A and 7B, when desired, a user may push the activation member 110 down to a second position (FIGS. 7A-8D) in which the activation member 110 pierces the foil element 100 to move the seal 20 to the open position (FIGS. 7A-8D). With the seal 20 in the open position, the vacuum 28 contained within the evacuated chamber 18 is applied to the inlet 30 and passageway 34 to draw a sample 12 within the collection chamber 16. In this manner, the vacuum 28 contained within the evacuated chamber 18 is placed in communication with the collection chamber 16 and passageway 34 of the biological fluid collection device 10 via the open aperture 102 and the vacuum 28 of the evacuated chamber 18 draws a sample 12 within the collection chamber 16 of the biological fluid collection device 10.

In one embodiment, a user may push the activation member 110 down to a second position (FIGS. 7A-8D) directly. In another embodiment, as shown in FIGS. 7A and 7B, the activation member 110 is disposed within the biological fluid collection device 10 between the second deformable portion 94 of primary housing 29 and the foil element 100 that seals aperture 102 within a wall of the evacuated chamber 18. In this manner, a user may push down the second deformable portion 94 so that the second deformable portion 94 contacts and pushes down the activation member 110 to the second position (FIGS. 7A-8D) in which the activation member 110 pierces the foil element 100 to move the seal 20 to the open position (FIGS. 7A-8D).

In one embodiment, the blood sample 12 fills the passageway 34 such that, as the blood sample 12 enters the biological fluid collection device 10, the blood sample 12 passes through the open cell foam, e.g., the material 70, and is exposed to the anticoagulant powder 74 available throughout the internal pore 72 structure of the open cell foam. In this manner, the sample 12 dissolves and mixes with the dry anticoagulant powder 74 while passing through the material 70 or open cell foam. Next, the mixing chamber 80 receives the sample 12 and the sample stabilizer 60 therein and effectuates distributed mixing of the sample stabilizer 60 within the sample 12 as described in detail above. After passing through the mixing chamber 80, the stabilized sample is directed to the collection chamber 16. The collection chamber 16 may take any suitable shape and size to store a sufficient volume of blood necessary for the desired testing, for example 500 µl or less.

In one embodiment, the cap 24 stops the collection of the blood sample 12 when the passageway 34, the mixing chamber 80, and the collection chamber 16 of the biological fluid collection device 10 has been fully filled. The venting portion 130 of the cap 24 allows air to pass through the cap 24 while preventing the blood sample 12 from passing through the cap 24.

Figure 8A:
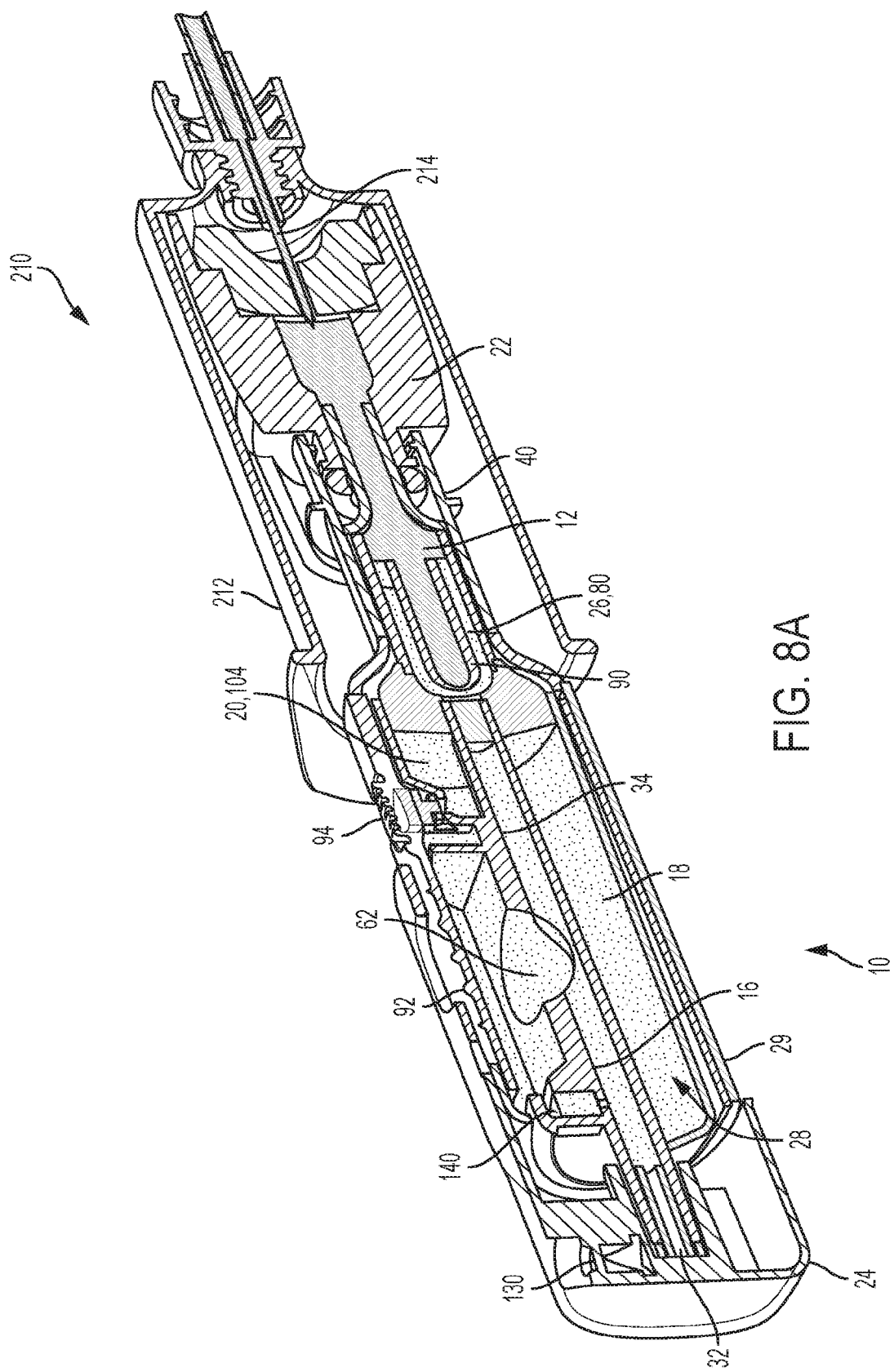
FIG. 8A is a cross-sectional side elevation view of a biological fluid collection device with a closure connected to a first blood collection device with a sample being drawn within a first portion of the biological fluid collection device in accordance with an embodiment of the present invention.
Figure 8B:
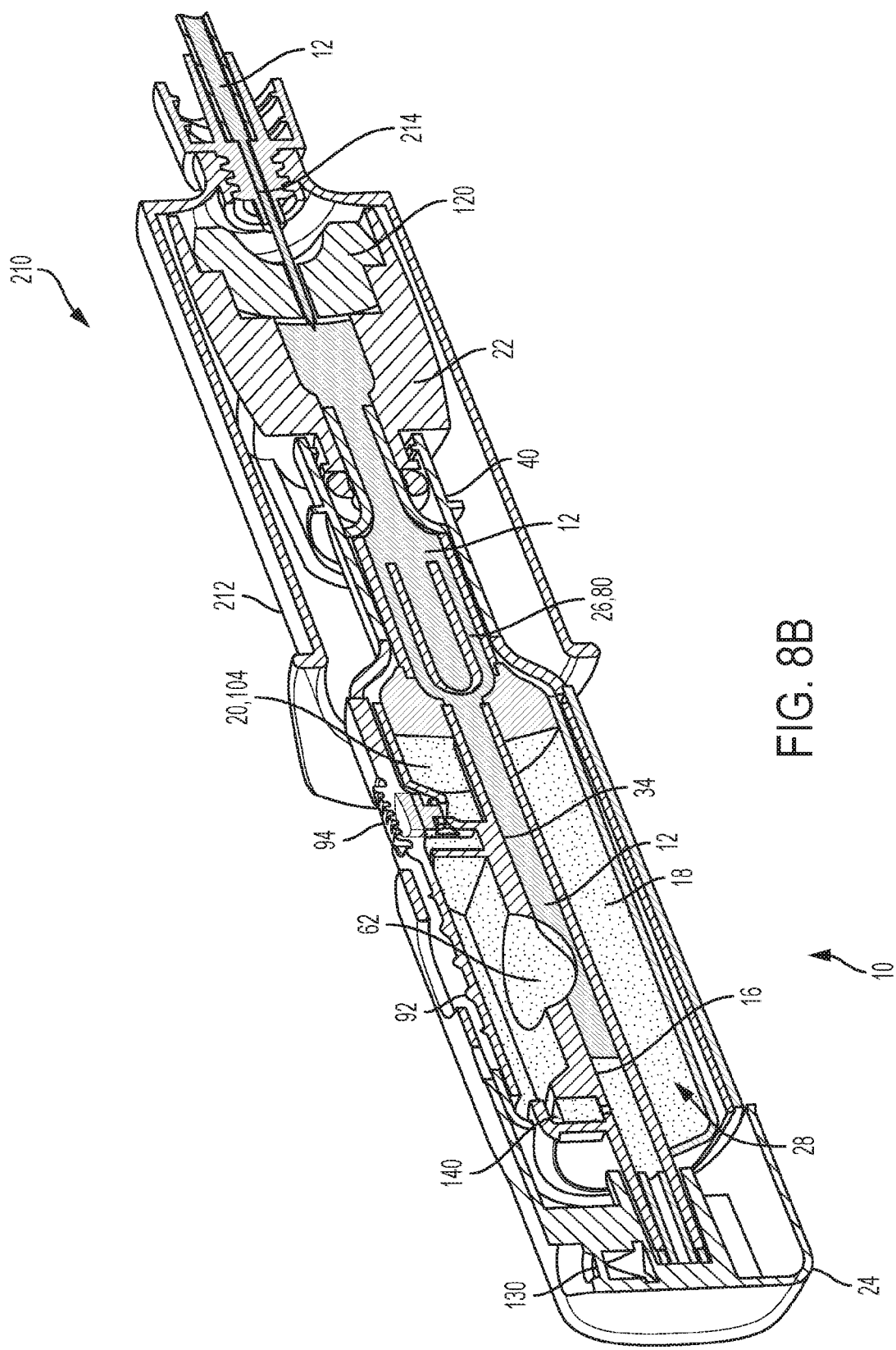
FIG. 8B is a cross-sectional side elevation view of a biological fluid collection device with a closure connected to a first blood collection device with a sample being drawn within a second portion of the biological fluid collection device in accordance with an embodiment of the present invention.
Figure 8C:
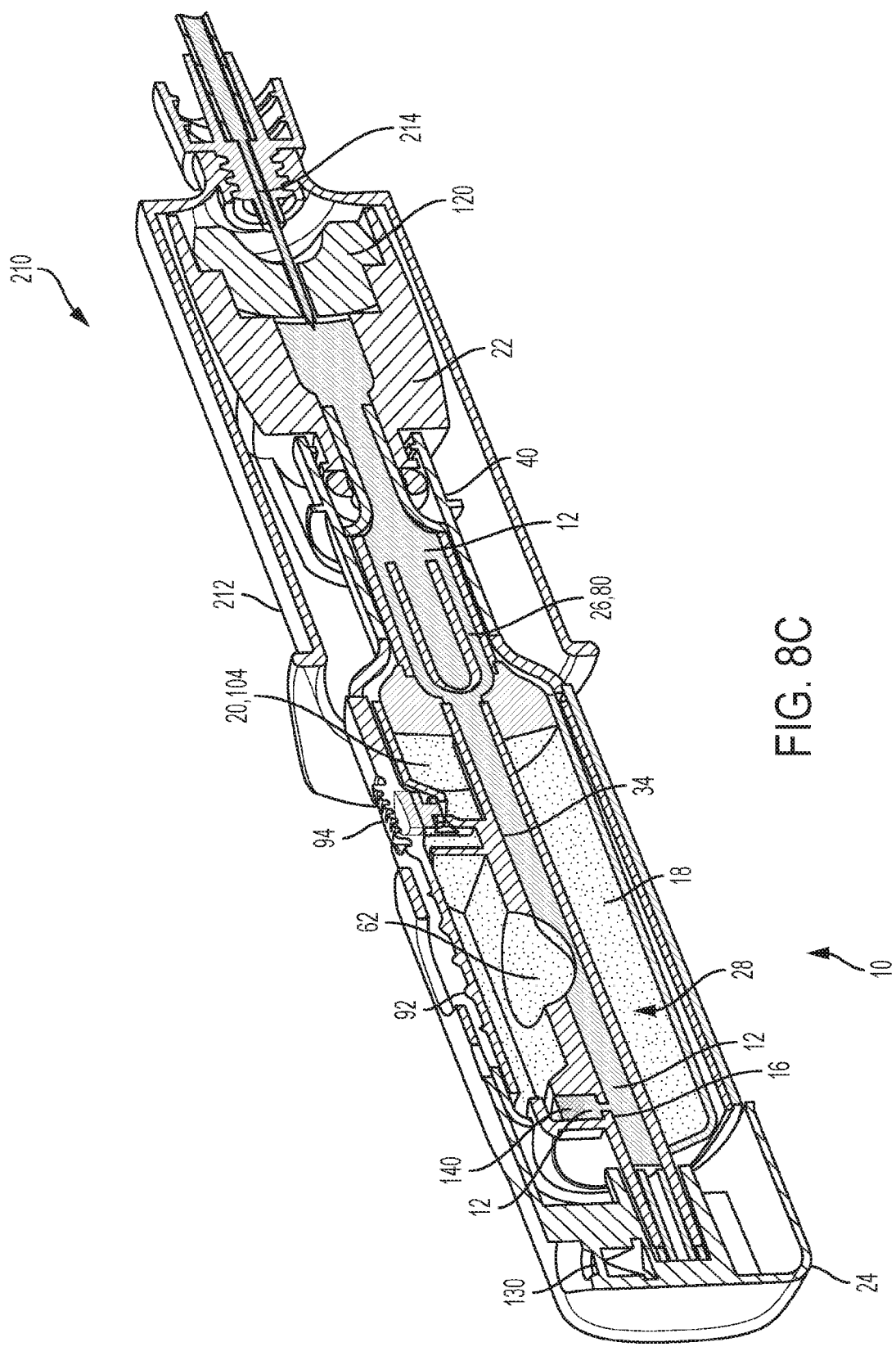
FIG. 8C is a cross-sectional side elevation view of a biological fluid collection device with a closure connected to a first blood collection device with a sample being drawn within a third portion of the biological fluid collection device in accordance with an embodiment of the present invention.

In one embodiment, the biological fluid collection device 10 also vents air as it fills with a blood sample 12. For example, in one embodiment, the design of the biological fluid collection device 10 is such that the resistance going through the plug 140 is less than, i.e., takes less energy than, it would take for the film 62 to rise. In this manner, air passes through and out the biological fluid collection device 10 via the plug 140 and/or the venting portion 130 of the cap 24 as the blood sample 12 begins to fill the biological fluid collection device 10 as shown in FIGS. 8A-8D. Air continues to pass through the plug 140 and/or the venting portion 130 of cap 24 and out of the biological fluid collection device 10 as the blood sample 12 continues to fill the biological fluid collection device 10. Referring to FIG. 8C, once the blood sample 12 fills the passageway 34 and the collection chamber 16, the blood sample 12 then wets out the plug 140, which seals off any fluid from moving through the plug 140. By venting any air within the biological fluid collection device 10 through the plug 140 and/or the venting portion 130 of the cap 24, all the possible air throughout the system is evacuated before the chamber 69 of the film 62 fills with blood or as the chamber 69 of the film 62 fills with blood.

Figure 8D:
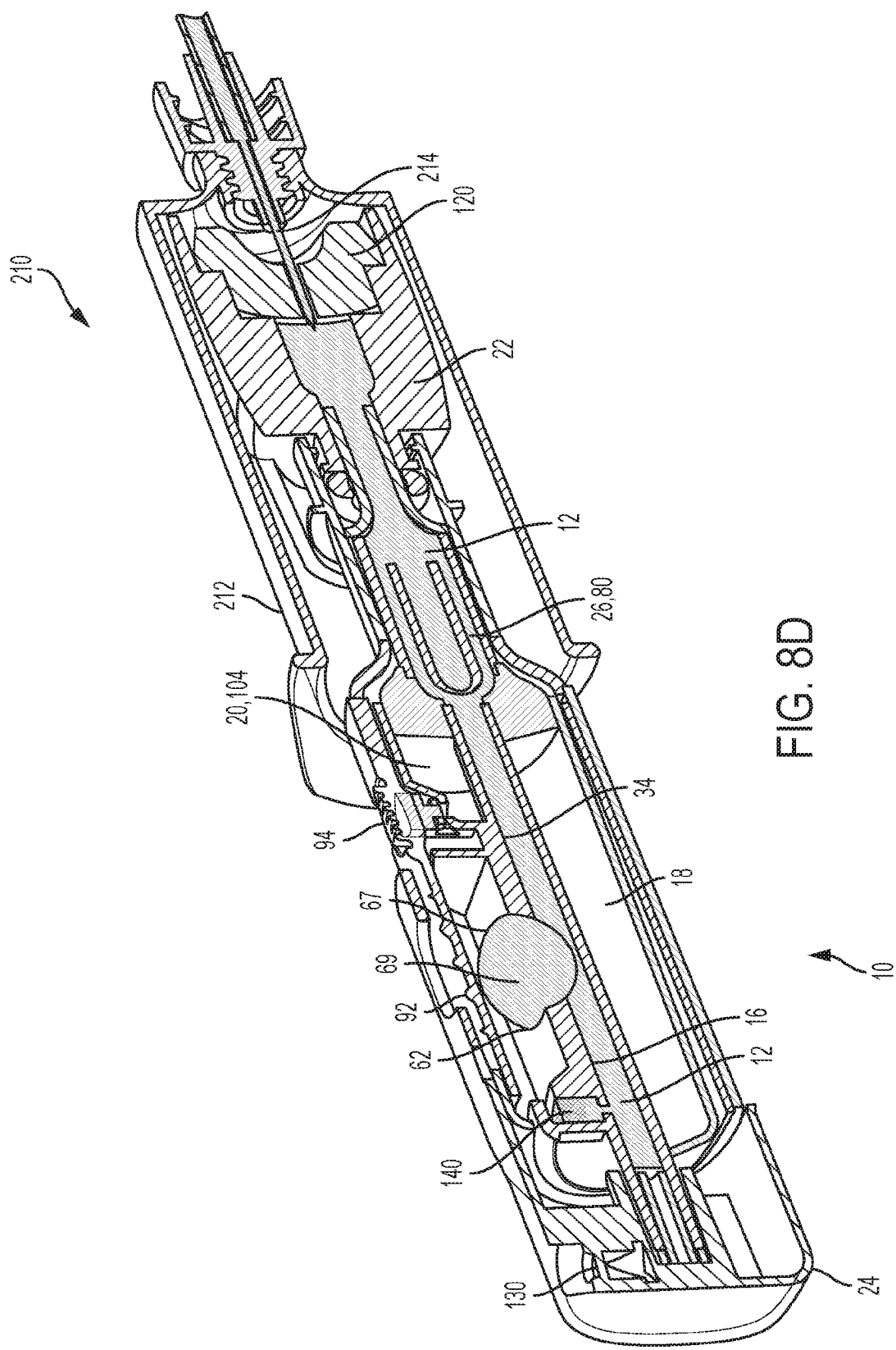
FIG. 8D is a cross-sectional side elevation view of a biological fluid collection device with a closure connected to a first blood collection device with a sample being drawn within a fourth portion of the biological fluid collection device and a film in a fill position in accordance with an embodiment of the present invention.

Referring to FIG. 8D, in one embodiment, after all the air has been exited from the biological fluid collection device 10 and the plug 140 has been wetted, the remaining vacuum 28 pulls the film 62 upwards, i.e., the remaining vacuum 28 transitions the film 62 from the initial position to a fill position (FIG. 8D). Referring to FIG. 8D, as the film 62 rises or is pulled up by the remaining vacuum 28 (because there is no air within the biological fluid collection device 10), a portion of the blood sample 12 is drawn into a chamber 69 that is located between the inferior surface 64 of the film 62 and the superior surface 54 of the cavity 52. The remaining vacuum 28 pulls the film 62 up until the chamber 69 is filled with a blood sample 12, as shown in FIG. 8D.

In one embodiment, once sample collection is complete, the biological fluid collection device 10 is separated from the tube holder 212. Next, referring to FIG. 9, the cap 24 is removed from the biological fluid collection device 10. The cap 24 is removed from the biological fluid collection device 10 exposing the outlet 32 of the housing 14. Removal may be accomplished by the user grasping an exterior portion of the cap 24 and pulling the cap 24 from the housing 14. The blood sample 12 is held within the passageway 34 of the housing 14, e.g., the collection chamber 16, by capillary action after removal of the cap 24.

The blood sample 12 may then be dispensed from the biological fluid collection device 10 by activation of the deformable portion 92. For example, the deformable portion 92 is transitionable between an initial position (FIG. 9) in which the sample 12 is contained within the collection chamber 16 and a deformed position (FIG. 10) in which the deformable portion 92 contacts the superior surface 66 of the film 62 and a portion of the sample 12 is expelled from the outlet 32 of the collection chamber 16.

In this manner, the blood sample 12 may be transferred to a device intended to analyze the sample, e.g., such as a point-of-care testing device, a cartridge tester, or a near patient testing device, while minimizing the exposure of the medical practitioner to the blood sample.

Figure 11:
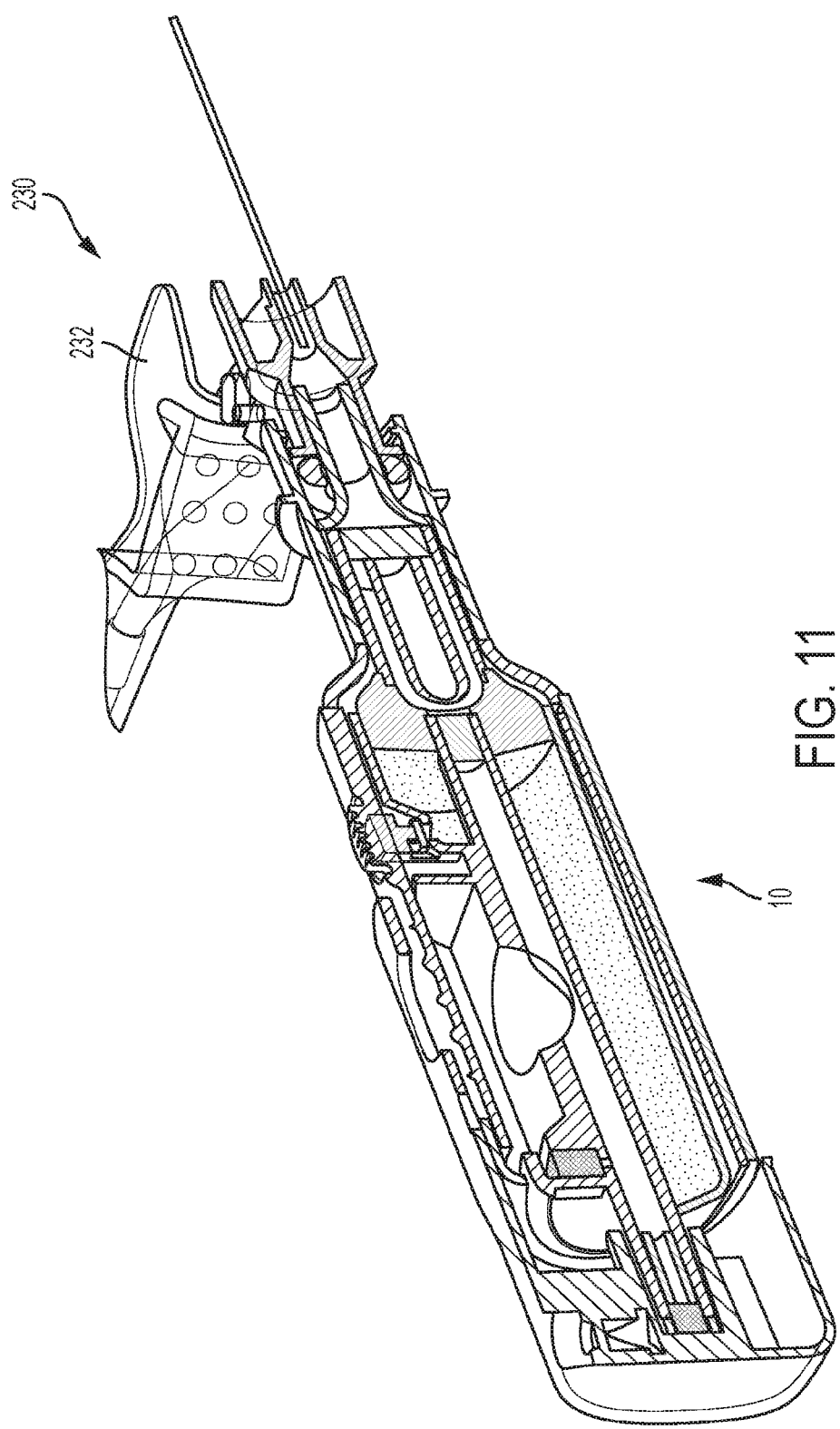
FIG. 11 is a cross-sectional side elevation view of a biological fluid collection device connected to a third blood collection device in accordance with an embodiment of the present invention.
Figure 12:
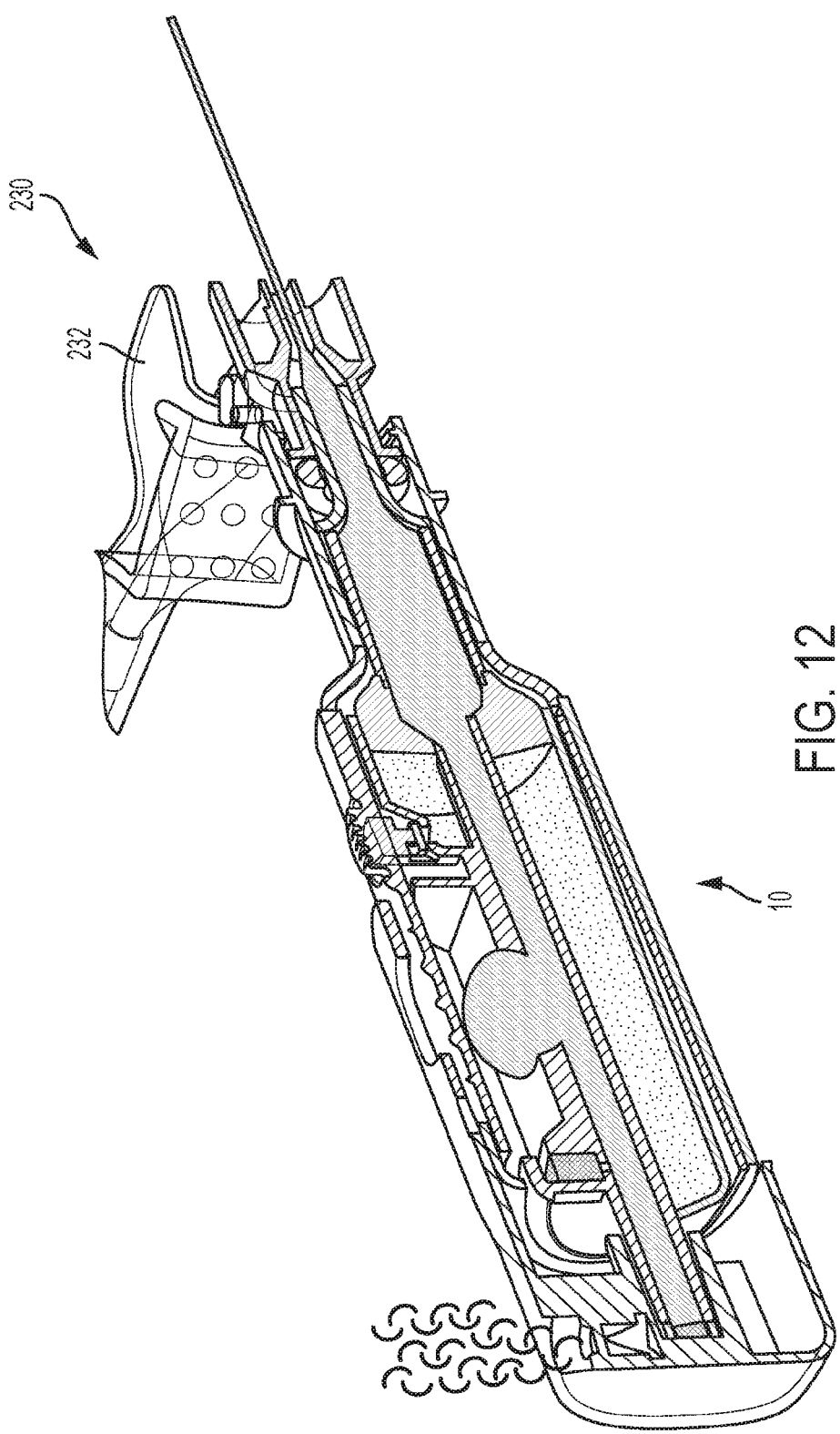
FIG. 12 is a cross-sectional side elevation view of a biological fluid collection device connected to a third blood collection device with a sample being drawn within the biological fluid collection device and a film in a fill position in accordance with an embodiment of the present invention.

Referring to FIGS. 4C and 11-12, in a third configuration, with a closure 22 removed from the housing 14 of the biological fluid collection device 10, the biological fluid collection device 10 may be connected to a third blood collection device 230. In one embodiment, the third blood collection device 230 includes an arterial blood collection device 232.

Use of a biological fluid collection device 10 connected to a third blood collection device 230 to receive a blood sample is similar to the use of a biological fluid collection device 10 connected to a first blood collection device 210, as described above with reference to FIGS. 5-10.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device adapted to receive a sample, the biological fluid collection device comprising:
   a housing having an inlet, an outlet, and a passageway extending between the inlet and the outlet;
   a collection chamber inside the housing and in fluid communication with the passageway;
   an evacuated chamber inside the housing and containing a vacuum; and
   a seal transitionable from a closed position in which the vacuum is enclosed within the evacuated chamber to an open position in which the vacuum is applied to the inlet to draw the sample within the collection chamber.

2. The biological fluid collection device of claim 1, wherein the seal comprises:
   a foil element disposed on a first portion of the collection chamber; and
   a stopper element disposed on a second portion of the collection chamber.

3. The biological fluid collection device of claim 2, further comprising an activation member transitionable between a first position and a second position in which the activation member pierces the foil element to move the seal to the open position.

4. The biological fluid collection device of claim 1, further comprising a closure covering the inlet of the housing.

5. The biological fluid collection device of claim 1, further comprising a cap covering the outlet of the housing and having a venting portion.

6. The biological fluid collection device of claim 5, wherein the venting portion allows air to pass therethrough and prevents the sample from passing therethrough.

7. The biological fluid collection device of claim 1, further comprising a film having an inferior surface and a superior surface, the film transitionable between an initial position in which the inferior surface of the film is in contact with a portion of the collection chamber and a fill position in which the inferior surface of the film is spaced from the collection chamber.

8. The biological fluid collection device of claim 7, wherein, with the film in the fill position, the collection chamber is filled with the sample.

9. The biological fluid collection device of claim 7, wherein, as the collection chamber fills with the sample, the film is transitioned to the fill position.

10. The biological fluid collection device of claim 7, further comprising a deformable portion transitionable between an initial position in which the sample is contained within the collection chamber and a deformed position in which the deformable portion contacts the superior surface of the film and a portion of the sample is expelled from the outlet of the collection chamber.

11. The biological fluid collection device of claim 1, further comprising:
   a mixing chamber disposed between the inlet and the collection chamber; and
   a sample stabilizer disposed between the inlet and the mixing chamber.

12. The biological fluid collection device of claim 11, wherein the mixing chamber receives the sample and the sample stabilizer therein.

13. The biological fluid collection device of claim 12, wherein the mixing chamber effectuates distributed mixing of the sample stabilizer within the sample.

14. The biological fluid collection device of claim 11, further comprising:
   a material including pores disposed between the inlet and the mixing chamber; and
   a dry anticoagulant powder within the pores of the material.

15. The biological fluid collection device of claim 14, wherein the sample dissolves and mixes with the dry anticoagulant powder while passing through the material.

16. The biological fluid collection device of claim 14, wherein the material is an open cell foam.

17. The biological fluid collection device of claim 14, wherein the sample stabilizer is the dry anticoagulant powder.

18. The biological fluid collection device of claim 1, wherein the sample is a blood sample.

* * * * *